US008257265B1

(12) United States Patent
Raju et al.

(10) Patent No.: US 8,257,265 B1
(45) Date of Patent: Sep. 4, 2012

(54) METHOD OF DIAGNOSING AND TREATING CVD

(76) Inventors: Seshadri Raju, Jackson, MS (US); Peter Neglen, Brandon, MS (US)

( * ) Notice: Subject to any disclaimer, the term of this patent is extended or adjusted under 35 U.S.C. 154(b) by 600 days.

(21) Appl. No.: 11/753,295

(22) Filed: May 24, 2007

(51) Int. Cl.
*A61B 8/00* (2006.01)
(52) U.S. Cl. .................. 600/462; 600/437; 600/459
(58) Field of Classification Search .................. 600/437, 600/459, 462
See application file for complete search history.

(56) References Cited

U.S. PATENT DOCUMENTS 7,615,018 B2 * 11/2009 Nelson et al. ................. 601/57
2004/0220607 A1 * 11/2004 Donovan et al. ............ 606/194

OTHER PUBLICATIONS

Seshardri Raju, "Recanalization of totally occluded iliac and adjacent venous segments", Feb. 2003, The Society for Vascular Surgery and The American Association for Vascular Surgery Published by Mosby, Inc., Journal of Vascular Surgery, vol. 36, Issue 5.*
Neglen et al., "Endovascular Surgery in the Treatment of Chronic Primary and Post-thrombotic Iliac Vein Obstruction", 2000, Eur Journal of Vascular Endovascular Surgery, 20, pp. 560-571.*
Peter Neglen and Seshadri Raju; Intravascular Ultrasound Scan Evaluation of the Obstructed Vein; Journal of Vascular Surgery; Apr. 2002; vol. 35, No. 4; pp. 694-700; United States.

* cited by examiner

*Primary Examiner* — Brian Casler
*Assistant Examiner* — Christopher Cook
(74) *Attorney, Agent, or Firm* — Jones, Walker, Waechter, Poitevent, Carrere & Denegre, LLP

(57) ABSTRACT

A method of diagnosing an obstructive lesion in the iliac venous system. The method includes the steps of identifying the presence of chronic venous disease from clinical evaluation alone of a patient, and without any further evaluation, undertaking an IVUS procedure on the patient to identify any non-thrombotic or thrombotic iliac vein lesions.

12 Claims, 2 Drawing Sheets

METHOD OF DIAGNOSING AND TREATING CVD

FIELD OF INVENTION

The invention relates to methods of diagnosing and treating venous disease.

BACKGROUND OF INVENTION

Patients with severe symptoms of chronic venous disease (i.e. with one or more following features: severe pain, swelling, (commonly clinically measured from grade 1 thru 3 representing pitting edema, (1) ankle edema (2) and gross swelling involving the limb (3), measured using a type of plethysmography) stasis dermatitis, venous ulcer) generally go through a battery of tests to determine the cause of disease, where testing includes duplex scans, venous function tests, ambulatory pressure measurements, arm/foot pressure tests, air plethysmography, contrast venography, CT venography and magnetic resonance venography. Clinical evaluation alone can be used to diagnose and grade severity of CVD, for instance, using the classes pursuant to clinical CEAP classification, such as C3-C6 scores for diagnosing more severe forms of CVD in the affected limb (C 0-2 an also be an indicator if severe symptoms of pain are present), but clinical evaluation alone cannot diagnose the pathology of the disease. Causes of CVD are generally attributable to obstruction (also called stenosis) or reflux or a combination. If a thrombotic or non-thrombotic vein lesion(s) causing venous obstruction or stenosis is diagnosed using the existing testing protocols (such as pressure measurements, duplex scans, venography and CT/MR imaging), then intravascular imaging techniques intravascular ultrasound (IVUS) can be used to determine the exact obstruction location and extent; percutaneous balloon angioplasty and/or stent placement is used to treat the obstruction at the same time. IVUS typically provides more detail of the obstructive lesion than venography and often the true extent of the lesion per IVUS is more severe than suggested by venography.

IVUS is a medical imaging methodology using a specially designed catheter with a miniaturized ultrasound probe attached to the distal end of it. The proximal end of the catheter is attached to computerized ultrasound equipment. Several companies manufacture and market this device. IVUS allows the application of ultrasound technology to image the vein wall including obstructive lesions. The physician positions the tip of a guidewire, such as a 0.32 inch guidewire (Glidewire, Terumo, Somerset, N.J.) with a very soft and pliable tip and about 200 cm long. The physician steers the guidewire from outside the body, though angiography catheters and into the blood vessel branch to be imaged. The ultrasound catheter tip (such as a 6F transducer) is slid in over the guidewire and positioned, within the vein of interest. The sound waves are emitted from the catheter tip, are usually in the 10-20 MHz range, and the catheter also receives and conducts the return echo information out to the external computerized ultrasound equipment which constructs and displays a real time ultrasound image of a thin section of the blood vessel currently surrounding the catheter tip, usually displayed at 30 frames/second image. A desired length of the vein can be imaged by slowly withdrawing the IVUS catheter over the guidewire.

The (a) blood vessel wall inner lining, (b) fibrosis within the wall and (c) connective tissues covering the outer surface of the blood vessel are echogenic, i.e. they return echoes making them visible on the ultrasound display. By contrast, the blood containing lumen itself is relatively echolucent, just black circular spaces, in the images.

The primary disadvantages of IVUS are its' expense, there is an increase in the time needed to perform the procedure, and the fact that it is an invasive interventional procedure. In the venous system, IVUS imaging techniques are generally not employed unless a diagnosis of obstruction is made using standard testing protocols (such as duplex, venography etc.). If obstruction is indicated, a single puncture provides the access for IVUS interrogation device (for instance, in the thigh area). A guidewire is used to insert the imaging catheter into the interior of the veins, and after the anatomy is defined with IVUS, the same guidewire is used for percutaneous stent placement. The procedure is usually performed in the operating room or angiography suite with the patient under general anesthesia though local anesthesia and intravenous sedation are acceptable in many patients.

SUMMARY OF THE INVENTION

The inventors have found that non-thrombotic iliac vein lesions (NIVL), which include webs and spurs (both considered types of obstructions), have a high prevalence and a broad demographic spectrum in patients with non-thrombotic chronic venous disease (CVD). NIVLs are infrequently found using standard testing protocols, but can be found more consistently using IVUS. However, IVUS would not normally be undertaken due to the lack of indication of obstruction from the traditional investigative protocol for CVD. The inventors propose using IVUS whenever significant symptoms of CVD are present, even when standard testing protocols indicate the lack of an obstruction (such as when venography does not indicate an obstruction). This applies both to non-thrombotic and post-thrombotic forms of obstruction, as IVUS will detect both. Hence, in the presence of severe pain (such as by having the patient assign a value between 0 (no pain) and 10 (extreme pain) with the value assigned being over 4-5, see *Graphic Representation of Pain*, Huskisson, Pain, 1976; 2:175-84), swelling, stasis dermatitis, or venous ulcer or a combination (severe pain alone, may be an indicator of CVD in about 10% of cases), the first procedure recommended is IVUS. If other testing is performed, but obstruction is not indicated, the inventors recommend that IVUS still be undertaken.

BRIEF DESCRIPTION OF THE DRAWINGS

FIG. 1A is a venogram of a segment of the iliac venous system.

FIGS. 1B, 1C and 1D are IVUS captured echograms of three areas of the segment of FIG. 1A.

FIGS. 1'B, 1'C and 1'D are hand drawn cartoon depictions of the echograms of FIGS. 1B, 1C and 1D respectively.

DETAILED DESCRIPTION OF THE INVENTION

Chronic venous disease (CVD) is commonly due to post-thrombotic disease or "primary" disease. Post-thrombotic disease is known to be due to a combination of obstruction and reflux. "Primary" disease is generally thought off as mostly due to reflux. The inventors have found that that iliac vein obstruction is a frequent component of "primary" disease as well. Obstruction in the iliac veins would generally be indicated on venography with the presence of visible stenoses and collaterals. The inventors have found that collaterals are present in only about one third of cases and stenotic areas are not frequently visible on venography. Routine use of IVUS can unmask many cases of occult stenoses and a stent placed to deal with the obstruction. While it is known that the iliac veins are a site for such obstructions, the obstructive component has been grossly underestimated as a significant cause of CVD. In the majority of the cases (both post-thrombotic and non-thrombotic, particularly the latter) where these obstructive indicative features are not present, the treatment has been directed towards treatment of reflux, where IVUS is not employed for diagnosis or visualization.

It has been known for some time, that in about 60% of the population, the left iliac vein harbors non-thrombotic iliac vein lesions (NIVL) where the right iliac artery crosses, where the lesion is due to either external compression or an internal web. The prevailing concept is that the lesion itself is benign—even a normal anatomical variation in most individuals and is a source of trouble in only a small minority. The prevailing view is that patients are generally young women and mostly the left leg is affected. The inventors consider the presence of NIVL lesions as "permissive" of symptom development, that is, in persons with this "permissive" lesion, any addition of trauma, infection or onset of additional venous pathology, such as reflux, results in symptomatic CVD (here, symptomatic of CVD means the presence one or more following features: pain, swelling, stasis dermatitis, venous ulcer). In others lacking the permissive lesion, additional trauma or pathology may not induce symptomatic CVD. Additionally, in some patients, the permissive lesion itself will progress in severity resulting in greater stenosis or narrowing of the iliac vein and produce symptoms of CVD without additional pathology.

Figure 1:
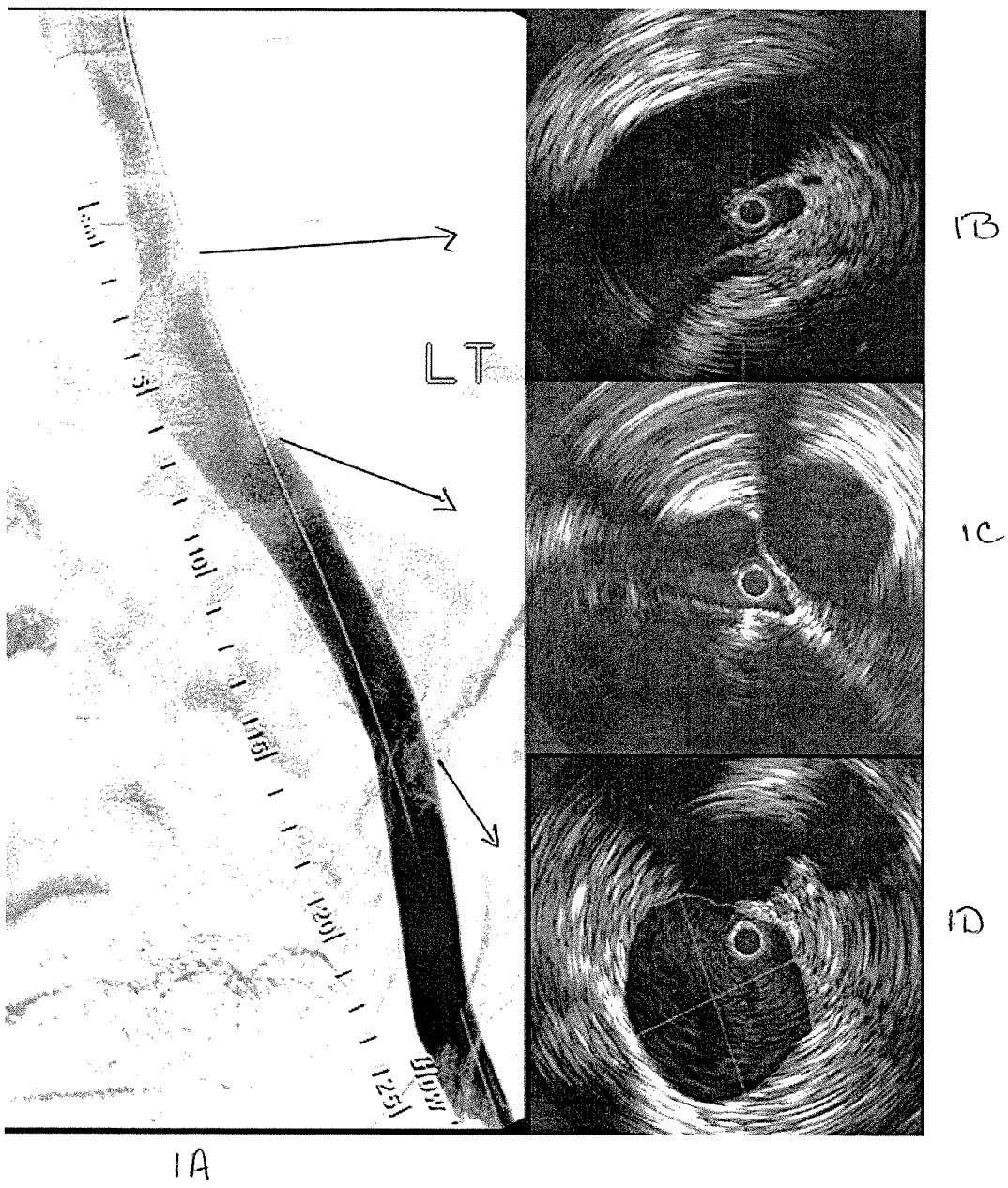
FIG. 1'A is a hand-drawn cartoon depiction of the venogram of FIG. 1A.
Figure 1:
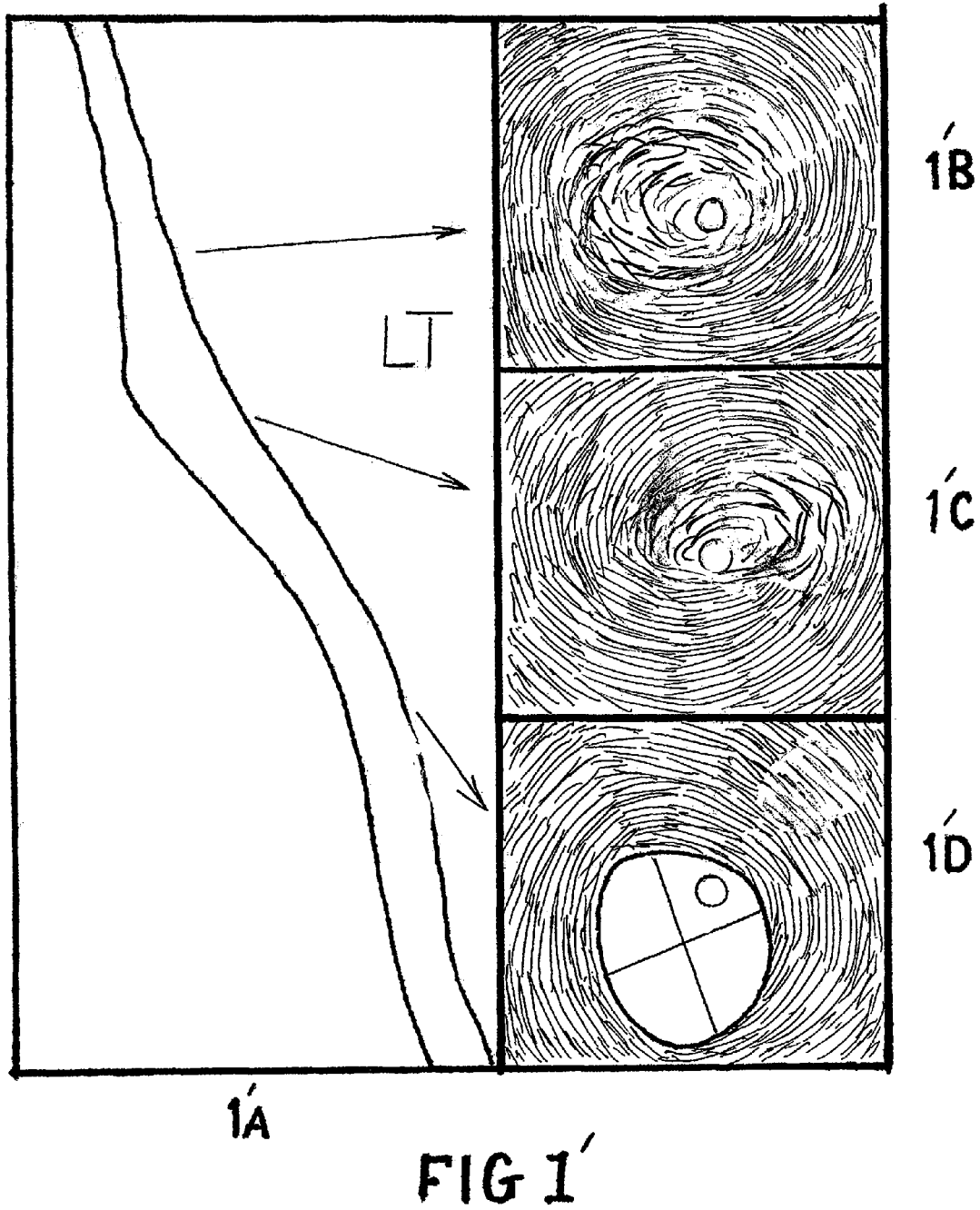

The inventors' studies have lead them to believe that >90% of non-thrombotic patients with symptoms of chronic venous disease harbor the obstructive permissive lesion, see *High prevalence of non-thrombotic iliac vein lesions in chronic venous disease: A permissive role in pathology*; Raju and Neglen, J. Vasc Surg 2006; 44:136-144 (hereby incorporated by reference) and such would not be readily detected using the usual testing protocol for evaluating CVD as the diagnosing sensitivity of venography or duplex for these permissive lesions is very poor. For instance, FIG. 1A shows a venogram of a segment of the iliac venous system. For ease of viewing, the venogram of FIG. 1A is reconstructed by hand drawn cartoon as FIG. 1'A. No portions of this segment are indicative of an obstruction. Shown in FIGS. 1B, 1C and 1D are IVUS echograms at three positions within the same segment. For ease of viewing, the IVUS echograms of FIGS. 1B, 1C and 1D are reconstructed by hand drawn cartoon as FIGS. 1'B, 1'C and 1'D respectively. As can be seen in FIG. 1D or 1'D, an obstruction is present, though not indicated by the venogram. Even if an obstruction is suggested by traditional techniques (primary venography or duplex), the severity of the lesion is grossly underestimated as the resolution of the techniques are poor, frequently leading to ignoring the lesion. The inventors believe that these cases should be evaluated by IVUS, even when traditional techniques suggest only a minor lesion. IVUS can uncover a significant lesion (>60% s stenosis) in most such cases. Further, permissive lesions can be found in men and women of all age groups, and these "permissive lesion" obstructions can be found, not only in the classic position (at the origin of the left iliac vein crossed by the artery), but in any location in the vein where compressive forces may be present. For instance, a frequent compression point is where the iliac vein is crossed by the hypogastric artery. Another compression location is where the vein is crossed by the inguinal ligament. The inventors have found that permissive stenoses occur in both sexes, in all age groups and on the right and left side lower limbs.

These permissive lesions are frequently not indicated by the conventional CVD testing protocol and even if found, are not generally considered lesions, but usually considered as normal anatomical variants. Investigation of chronic venous disease, particularly of "primary" aetiology, with IVUS for a "permissive" lesion is a new testing protocol proposed. We propose that the use of IVUS will detect lesions not seen on venography, and that stenting be done to correct the lesion, yielding results comparable with the traditional treatment of CVD without the indication of obstruction, that being correction of reflux. Additionally, the suggested diagnosis and treatment method (IVUS diagnosis and venous stent placement) is a percutaneous procedure, whereas correction of deep venous reflux requires an open procedure at the present time. The inventors further propose that IVUS examination be undertaken in post-thrombotic cases even if the venogram or other traditional diagnostic technique does not suggest a significant iliac vein obstruction or stenosis. IVUS will detect either a permissive lesion that triggered the thrombosis or a post-thrombotic lesion resulting from the thrombosis will become evident. Such lesions should be stented and the patients may benefit without additional procedures, such as for example, correction of reflux.

The inventors propose that when symptoms of CVD are present, that intravascular ultrasound (IVUS) examination be the primary tool for diagnosis, undertaken on the iliac veins and the adjacent venous segments on the affected side (for definition purposes, the iliac venous system includes the common internal and external iliac veins and the inferior vena cava and the common femoral and femoral vein, (particularly the adjacent segments of the inferior vena cava and common femoral and femoral). NIVL lesions are readily visible through IVUS as subsegmental and focal (<2 cm), and occur near arterial crossover points near the upper or lower ends of the vein segment, finally, the wall thickness and lumen size of the rest of the vein segment are normal. NIVL lesions are considered significant (requiring stenting) if the lumen size is stenosed by about 40%, more preferably about 50% (as measured by cross sectional area (or about a 30% reduction in the radius or diameter for 50% cross-sectional area reduction)) or more (as compared to adjacent segments) by the lesion which is readily determined by IVUS area measurement software included with IVUS machines. In contrast, post-thrombic disease lesions (those generally visualizable using venography, but not necessarily) are segmental, involving at least one entire segment and often adjacent segments. Contrawise, post-thrombic disease lesions are irregular, multiple and diffuse with wall fibrosis and lumen stenosis in the entire segment; trabeculae may also be present. If a permissive lesion is found (studies indicated that such will be found in over 90% of non-thrombotic cases so examined), the lesion may be balloon dilated if needed, and the inventors believe a venous stent should be placed to correct the lesion (such as with a 14-16 mm Wallstent, from Boston Scientific). The inventors believe that balloon dilation alone is generally insufficient as it is not durable and that it is preferred, in all iliac vein lesions, whether thrombotic or non-thrombotic, to undertake stenting immediately after balloon dilatation. Stenting should be over a sufficient length to cover the entire lesion. (See *Recanalization of totally occluded iliac and adjacent venous segments*, Raju, McAllisaer and Neglen, J. Vasc Surg. 2002, 36:903-911, hereby incorporated by reference.)

The stenting technique is as follows: the femoral vein is punctured at mid or upper thigh level (the preferred location) which allows ample room for stenting to be done below the groin crease, even after placement of a sheath. Sheaths are plastic tubes with one way valves that are routinely placed after vascular puncture to facilitate passage of guidewires, catheters, IVUS probes etc. The valve allows forward passage of such devices but prevents back bleeding from the vessel. The standard practice is to puncture vessels at points where they are close to the surface where they can be compressed easily for a period of time after the sheath is removed to stop bleeding from the puncture hole in the vessel. The inventors have found that veins, particularly the femoral vein can be punctured at deep locations, such as at mid thigh level, as they have low pressure and the bleeding from the puncture hole can be stopped by putting pressure on the vein even over deep locations. Puncture sealing devices can also be used. This has distinct advantage as the patient can be positioned supine. The traditional approach would be to puncture the popliteal vein in the prone position which limits pushability and torqueability of devices passed through the sheath, these limitations are reduced with the inventors' approach. Another traditional approach is to puncture the femoral vein near the groin where the vein is superficial and is easily compressed. This, however, prevents stents being deployed below the groin, as is often necessary; as the sheath extends well above the groin in such an approach. The IVUS catheter is introduced through the sheath and the iliac vein and adjoining segments are examined under fluoroscopy. NIVL or thrombotic lesions that produce stenoses are noted and their position marked under fluoroscopy. A venogram may be done as an aid to localization as well, but is not essential. If any one or more of the lesions are found to produce greater than 60% lumen stenosis, all of the lesions will require to be balloon dilated and stent(s) placed. The traditional approach is to place the stents in the iliac veins without encroaching upon the inferior vena cava for fear of obstructing it. The inventors have found that the stents should be extended into the inferior vena cava, otherwise recurrence of stenosis at the entry of the iliac vein into the inferior vena cava occurs. The inventors have found that extension of the stent into the inferior vena cava does not obstruct the opposite iliac vein flow. The inventors have also found that only large stents, 14 mm or larger, should be placed in the iliac veins; smaller stents do not allow for adequate flow and may clot. The traditional approach is not to extend the stents across the groin crease line for fear of stent fracture, compression or erosion of the blood vessel due to bending and unbending of the stent across the groin crease. This fear is based on adverse experience with stents crossing the joint lines in the arterial system. The inventors have found that such adverse events do not occur with "Wall" stents and other stents crossing the groin crease. The inventors have found that stents should be extended in such a manner to treat all diseased areas in the iliac and adjacent inferior vena cava and femoral vein segments. The inventors have found that skip areas, areas without stent coverage, should not be left and that all lesions should be covered by stent(s) in continuity. Failure to extend the stent into the femoral vein when required to cover all stenotic areas, such as for example, when stenosis is present behind the inguinal ligament, results in malfunction or thrombosis of the stent (as found by the inventors). The inventors have found that anticoagulation with warfarin is not necessary in NIVL cases and aspirin treatment alone suffices, except occasionally when the patient suffers from thrombophilia. Thrombophila is propensity of the patient to develop blood clots due to abnormalities of the blood clotting mechanisms. When both legs (right and left) have to be stented, the inventors have found it necessary to fenestrate the existing stent so that the opposite stent being introduced can be connected or hooked or joined to it. Fenestration is created by introducing a balloon over a guide wire passed through the side of the braided stent and distending the balloon to create an opening or fenestration. The opposite newer stent is introduced into the fenestration to connect with it producing an inverted 'Y' appearance with the lower limbs filling the iliac veins and the conjoint top portion occupying the vena cava. This is the procedure of choice when the opposite stent is introduced after the first stent has been in place for more than a week. If bilateral stents are introduced at the same time, a double barrel technique can be used, allowing the two stents to lie side by side in the vena cava without the fenestration procedure. When one stent has been in place for a week or more, the double barrel technique will not work because, as found by the inventors, the old stent will compress the new stent. See *Combined saphenous ablation and the iliac stent placement for complex severe chronic venous disease*, Neglen, Hollis, Raju, J. Vasc Surg; 2006:44:828-33).

In post-thrombotic disease, the iliac veins, the femoral vein and the inferior vena cava can be totally occluded in segments or in continuity. The inferior vena cava can be occluded segmentally in the infra renal portion, in the supra renal portion or in the thoracic portion or in continuity. The inventors have found that these substantially total occlusions at the various locations, whether segmental or in continuity, can be "recanalized" by (1) manipulation of the guide wire through the occlusions and then (2) enlarge the guidewire channel by balloon dilation. The inventors have found that the channel can be dilated up to 25 mm in the inferior vena cava, 16-18 mm in the common iliac vein, 14-16 mm in the external iliac vein and 12-14 mm in the femoral vein without fear of vein rupture and clinical hemorrhage. This allows large sized stents as indicated in correcting non-occlusive stenosis to be placed after recanalization of occluded inferior vena cava, iliac and femoral veins. The inventors have found that renal or hepatic impairment are very rare after such extensive stenting which crosses the renal and hepatic vein drainage pathways. See *Obstructive lesions of the inferior vena cava: Clinical features and endovenous treatment*, Raju, Hollisand Neglen, J. Vasc Surg 2006; 44:820-7 (hereby incorporated by reference).

In the studies performed by the inventors, over half the patients so treated (stenting of stenoses and stenting with recanalizations) will have sustained relief of symptom(s) beyond 5 years. The treatment offered is also novel way of treating venous reflux as the inventors have found that this treatment will improve, by measurement (hemodynamic parameters of reflux, specifically ambulatory venous pressure and airplethysmography parameters of reflux) and the symptoms of reflux (pain, swelling, stasis dermatitis, venous ulcer) will be relieved in the majority of patients. Contrary to prevailing opinions, the inventors have found that preexisting reflux is not worsened by correcting the obstructive component with a stent. The inventor's studies have shown that correction of the permissive lesion by a venous stent can yield sustained symptom relief beyond 5 years in over 50% of patients.

Previously, the traditional way to treat these patients was with a veno-venous bypass when a severe obstruction was indicated or, lacking indications of obstruction to correct the reflux component by ablation of the saphenous vein, correction of perforator reflux and/or repair of refluxive deep valves according to individual pathology in each cases. Additionally, the inventors propose that the diagnosis of a permissive lesion using IVUS imaging techniques, and subsequent treatment of such with a stent can be combined with simultaneous ablation of saphenous vein by a percutaneous technique, such as with laser or radiofrequency heat (a well known technique in the art). The combination stent/ablation will result in a total percutaneous procedure relieving both obstruction and reflux simultaneously. Using this combined treatment, deep or perforator reflux is left untreated, but the inventors' studies indicate that stent placement alone or when combined with saphenous ablation, improves hemodynamic parameters of reflux, specifically ambulatory venous pressure and air plethysmography parameters of reflux. Parameters of obstruction, particularly arm/foot venous pressure are improved by the stent procedure.

The invention claimed is:

1. A method of diagnosing an obstructive lesion in the iliac venous system, comprising the steps of
   a. non-invasively diagnosing from clinical evaluation alone the presence of chronic venous disease ("CVD") in a patient, where said clinical evaluation consists of evaluation of one or more of pain, swelling, stasis dermatitis, or venous ulcer and
   b. performing an intravascular ultrasound ("IVUS") procedure on said patient's venous system to
   c. identify any non-thrombotic or thrombotic iliac venous system lesions,
   d. where said IVUS procedure is performed prior to undertaking other procedures to test said CVD diagnosis where said other procedures consists of one or more of the following: a duplex scan, contrast venography, computed tomography (CT) venography, and magnetic resonance venography.

2. The method of claim 1 further comprising the steps of treating at least one of said identified non-thrombotic or thrombotic iliac vein lesions by stenting said lesions.

3. The method of claim 2 wherein all of said identified lesions are treated by stenting, and all areas between the identified lesions are also treated by stenting.

4. The method of claim 2 wherein said IVUS procedure is initiated at the femoral vein punctured at the mid or upper thigh level of a patient.

5. The method of claim 2 further including the step of balloon dilating each stented non-thrombotic or thrombotic iliac venous lesions prior to stenting.

6. The method of claim 2 wherein said stenting uses stents of diameter about 12-24 mm.

7. The method of claim 1 wherein the steps of identifying non-thrombotic or thrombotic iliac vein lesions includes the steps of identifying subsegmental and focal (about <2 cm) segments of the iliac vein that evidence stenoses.

8. The method of claim 7 wherein the steps of identifying non-thrombotic or thrombotic iliac vein lesions includes the steps of identifying wall fibrosis.

9. The method of claim 1 wherein said step of identifying any non-thrombotic or thrombotic iliac venous system lesions includes the steps of identifying segments where stenoses is greater than about 40% of said surrounding segments, as measured by cross-sectional area.

10. The method of claim 9 wherein said stenoses is greater than about 98%.

11. The method of claim 10 further comprising the steps of treating said stenoses by recanalization.

12. A method of diagnosing an obstructive lesion in the iliac venous system, comprising the steps of
   a. non-invasively diagnosing from clinical evaluation alone the presence of chronic venous disease ("CVD") in a patient, where said clinical evaluation consists of evaluation of one or more of pain, swelling, stasis dermatitis, or venous ulcer and
   b. performing an intravascular ultrasound ("IVUS") procedure on said patient's venous system to
   c. identify any non-thrombotic or thrombotic iliac venous system lesions, where said IVUS procedure is the first procedure performed to test said CVD diagnosis.

* * * * *